United States Patent
Prabhakar et al.

(10) Patent No.: US 7,259,148 B2
(45) Date of Patent: Aug. 21, 2007

(54) HEPATOPROTECTIVE ACTIVITY OF 2'-P-HYDROXYBENZOYLMUSSAENOSIDIC ACID

(75) Inventors: Anil Prabhakar, Jammu (IN); Bishan Datt Gupta, Jammu (IN); Krishan Avtar Suri, Jammu (IN); Naresh Kumar Satti, Jammu (IN); Swadesh Malhotra, Jammu (IN); Kuldip Kumar Gupta, Jammu (IN); Vijay Kumar Sharma, Jammu (IN); Rakesh Kamal Johri, Jammu (IN); Bupinder Singh Jaggi, Jammu (IN); Bal Krishan Chandan, Jammu (IN); Shankar Lal, Jammu (IN); Kasturi Lal Bedi, Jammu (IN); Om Parkash Suri, Jammu (IN); Gulam Nabi Qazi, Jammu (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/436,321

(22) Filed: May 12, 2003

(65) Prior Publication Data

US 2004/0014684 A1    Jan. 22, 2004

(51) Int. Cl.
*A61K 31/70* (2006.01)
(52) U.S. Cl. ..................................... 514/27
(58) Field of Classification Search ............... 514/27, 514/4.1, 18.1; 536/4.1, 18.1
See application file for complete search history.

(56) References Cited

U.S. PATENT DOCUMENTS 6,664,236 B2 * 12/2003 Suri et al. ..................... 514/27

OTHER PUBLICATIONS

Healh-cares.net., pp. 1-5, Dec. 14, 2006.*
The Merck Manual of Geriatrics on line, pp. 1-3, Dec. 15, 2006.*
Subramoniam, A., et al., "Development of Phytomedicines for Liver Disease," *Indian Journal of Pharmacology*, 1999, vol. 35, pp. 166-175.
Ansari, R.A., et al., "Hepatoprotective activity of kutkin-the iridoid glycoside mixture of *Picrorhiza kurrooa*," *Indian J. Med Res*, 1988, vol. 87, pp. 401-404.
Dutta, P., K., et al., Studies on Indian Medicinal Plants-Part LXXV[1] Nishindaside, a Novel Iridoid Glycoside from Glycoside from *Vitex negundo*, Indian Institute of Chemical Biology, 1983, vol. 39, pp. 3067-3072.
Sehgal, C. K., et al., "2'-p-Hydroxybenzoyl mussaenosidic acid, a new iridoid glucoside from vitex negundo," *Phytochemical*, 1982, vol. 21, pp. 363-366.
Abstract. Hansel, Ch., et al., "Chemtaxonomische untersuchungen in der gattung vitex I.*," *Phytochemical*, 1965, vol. 4, pp. 363-366.
Vishnoi, S. P., et al., A Furanoeremophilane from *Vitex negundo*, *Phytochemical*, 1983, vol. 22, pp. 597-598.
Chawla, A. S., et al., "Chemical investigation and anti-inflammatory activity of *Vitex negundo* Seeds," *Journal of Natural Products*, 1992, vol. 55, pp. 163-167.
Chawla, A. S., et al., "Chemical investigation and anti-inflammatory activity of *Vitex negundo* seeds: Part I," *Indian Journal of Chemistry*, 1991, vol. 30B, pp. 773-776.
Chawla, A. S., et al., "Flavonoids of *Vitex negundo*," *Journal of Natural Products*, 1979, vol. 42, pp. 540-542.
Subramanian, P. M., et al., "Leucoanthocyanidins of *Vitex negundo*," *Indian Journal of Chemistry*, 1978, vol. 16B, pp. 615-616.
Rao, U. K., et al., "Phenolic Constituents of the Bark of *Vitex negundo*," *Indian Journal of Chemistry*, 1977, p. 41.
Abstract. Hansel, R., et al., "Chemtaxonomishe Untersuchungen in Der Gattung *Vitex l.*,*" *Phytochemistry*, 1965, vol. 4, pp. 19-27.
Banerji, A., et al. "Isolation of 5-Hydroxy-3,6,7,3', 4'-Pentamethoxy Flavone From *Vitex negundo*," *Phytochemistry*, 1969, vol. 8, pp. 511-512.
Banerji, J., et al., "Isolation of 4,4'-Dimethoxy-*trans*-stilbene & Flavonoids from Leaves and Twigs of *Vitex negundo* Linn.," *Indian Journal of Chemistry*, 1988, vol. 27B, pp. 597-599.
Ghose, T. P., et al., "Constituents of the Leaves of *Vitex negundo*," Journal of , 1936, vol. 13, pp. 634-640.
Abstract. Sirait, L. M., et al., Flavoinde aus *Vitex agnus castus* L., *Expendentia*, 1962, vol. 18, p. 72.
Abstract. Chopra, R. N., Glossary of Med. Plant, 1956, p. 256.
Abstract. Wealth of India, Raw Material, 1976, vol. 5, p. 522.
Achari, B., et al., "Two Isomeric Flavanones from *Vitex negundo*,*" *Phytochemistry*, 1984, vol. 23, pp. 703-704.

* cited by examiner

*Primary Examiner*—Elli Peselev
(74) *Attorney, Agent, or Firm*—Morgan & Finnegan, L.L.P.

(57) ABSTRACT

The present invention provides a method for treating and/or preventing hepatic disease conditions in a subject mammals including human beings, said method comprising the steps of administering to the mammal an effective dosage of composition comprising 2'-p-Hydroxy benzoyl mussaenosidic acid from plant *Vitex negundo* optionally as individual or in combination with one or more pharmaceutically additives.

16 Claims, 2 Drawing Sheets

1

Negundoside

Flowsheet for isolation of 2'-p-hydroxybenzoylmussaenosidic (negundoside)

HEPATOPROTECTIVE ACTIVITY OF 2'-P-HYDROXYBENZOYLMUSSAENOSIDIC ACID

FIELD OF THE INVENTION

This invention relates to hepatoprotective activity of an iridoid glycoside, 2'-p-hydroxybenzoylmussaenosidic acid (negundoside) of the formula 1 isolated from *Vitex negundo* by extracting the aerial parts/whole plant with polar solvents like methanol, ethanol aqueous ethanol or water, removing fatty non polar constituents by triturating the extracts solvents such as hexane, ethylene chloride, methylene chloride, chloroform or ethyl acetate to get a fraction from which negundoside is separated by column chromatography. The hepatoprotective activity of negundoside has been confirmed by evaluation of its protective action against CCU and galactosamine induced liver damage models. Background and Prior art references *Vitex negundo* Linn (family: Verbenaceae) is widely used in the indigenous system of medicine in India. The leaves of the plant are constituents of several preparations used in Ayurvedic system of medicine. The roots and leaves of the plant are used as expectorant, febrifuge, vermifuge tonic and aromatic [Chopra, R. N. Nayar, S. L. and Chopra I. C ; Glossary of Indian Medicinal Plants, CSIR, New Delhi,. 1956, p. 256].

BACKGROUND ART

The plant is reported to have anti-inflammatory and antiarthritic properties. [Wealth of India: Raw Materials, CSIR, New Delhi, 1976, vol. X, p. 522]. A variety of constituents have been reported from this plant. From the leaves Ghosh and Krishna isolated glucononitol, p-hydroxybenzoic acid, 5-hydroxyisophthalic acid and 3,4-dihydroxybenzoic acid along with two glucosides and an amorphous alkaloid [Ghosh, T. P. and Krishna, S., *Indian Chem.* 1936, 13, 634] In the essential oil of leaves a-pinene, camphene, citral and (3-caryophyllene have been reported [Masilungan, V. A., *Philip. J. Sci,* 1955, 84, 275].

A large number of flavonoids viz., casticin, orientin, isoorientin, luteolin, luteolin-7-0-glucoside, corymbosin, gardenins A and B, 3-0-desmethylartemetin,5-0-desmethylnobiletin,3\4\5,5\6J,8-heptamethoxyflavanone and 3\,5-dihydroxy-4',6,7-trimethoxy flavanone and 3',5-dihydroxy-4', 6,7-trimethoxyflavanone have been reported from this plant [Sirait, L. M., Rimpler, H. and Haensal, R., *Experientia* 1962, 18, 72; Haensal, R. et al. *Phytochemistry* 1965, 4 ,19; Banerji A. et al. *Phytochemistry* 1969, 8,511; Ferdous, A. J. et al. *Bangladesh Acad. Sci.* 1984, 8,23; Dayrit, F. M. et al. *Philipp. J. Sci.* 1987, 116, 403; Banerji, J. et al. *Indian J. Chem.* 1988; 27B, 597; Achari, B. et al. *Phytochemistry.* 1984, 23, 703]. Stem-bark afforded five new flavone glycosides along with luteolin and acerosin. The new flavone glycosides are 6p-glucopyranosyl-7-hydroxy-3',4',5',8-tetramethoxyflavone-5-O-α-L-rhamnopyranoside, 3',7-dihydroxy-4',6,8-trimethoxyflavone-5-O-(6"-O-acetyl-p-D-glucopyranoside),3,3',4',6,7,-pentamethoxyflavone 5'-O-(4"-O-β-D-glucopyranosyl-cc-rhamnopyranoside, 4',5,7-trihydroxyflavone-8-(2"-caffeoyl-a-glucopyranoside) and 3',5, 5',7-tetrahydroxy-4-methoxyflavone -3'-O-(4"-O-α-D-galactopyranosyl) galactopyranoside [Rao, V. K. et al. *Indian J. Pharm.* 1977,39, 41; Subramamian, P. M. and Misra, G. S. *Indian J. Chem.* 1978, 16B, 615; Subramaniam, P. M. and Misra, G. S. *J. Nat. Prod.* 1979,42, 540]. A diterpenoid, 5β-hydro-8,11,13-abieta-trien-6a-ol and three triterpenoids, 2 cc, 3a-dihydroxyoleana-5 12-dien-28-oic acid, 2a, 3a-diacetoxyoleana-5, 12-dien-28-oic acid, 2,3 a-diacetoxy-18-hydroxyoleana-5,12-dien-28-oib acid have been isolated from the seeds, These compounds exhibited antiinflammatory activity [Chawla, A. S., Sharma, A. K., Handa, S. S. and Dhar, K. L. *Indian J. Chem.* 1991, 30B, 773 and *J. Nat. Prod.* 1992,55,163. From the roots acetyloleanolic acid was isolated [Vishnol, S. P., Shoeb, A., Kapil, R. S. and Popli, S. P. *Phytochemistry* 1983, 22, 597].

Five Iridoid glycosides have been reported from the leaves of *V. negundo*. These areaucubin, agnuside (Hansal et al. *Phytochemistry* 4, 1965, 9) negundoside, 6'-hydroxyhenzoyl mussaenosidic acid (Sehgal et al. *Phytochemistry,* 21, 1982, 363) and nishindaside (Datta et al. *Tetrahedron* 39, 1983, 3067).

Liver disorders are still the major hazard both in urban and rural population. Despite scientific advances in our understandings in the management of liver disorders and the leads provided by traditional system of medicine, no specific treatment of liver ailments is available except chemically undefined a few herbal formulations [Subeamonium and Puspagandan, *Indian Journal of Pharmacology,* 31, 166-175 (199)]. During our search for hepatoprotective agents of plant origin, the aqueous alcoholic extract of *V. negundo* and a fraction isolated from its exhibited strong hepatoprotective and immunostimulating activities. A process has been developed for isolation of fraction possessing immunostimulating activity from the leaves of *V. negundo* for which a patent has been granted to Regional Research Laboratory, Jammu [Sun, J. L. et. al Indian Patent No. 178388 dt. 19-03-97). Another patent application has been submitted by Regional Research Laboratory, Jammu for a process for isolation of a bioactive composition possessing hepatoprotective and immunostimulating activity (Application no. 116/DEL98 dt. 16.1.98). iridoid glycosides of *Picrorhiza kurroa* exhibit strong hepatoprotective activity {Ansari, R. A. et al., *Indian J. Med. Research* 1988, 87, 401). *V. negundo* has also been found to contain a number of iridoid glycosides. An iridoid glycosides. 2'-p-hydroxybenzoylmussaenosidic acid (negundoside) was isolated and evaluated for its hepatoprotective activity along with the alcoholic extract of the plant. Both alcoholic extract (coded as 033) and negundoside (coded as 033 (2)) showed marked hepatoprotective activity in experimentally induced hepatic damage with $CCl_4$ and galactosamine (GaIN) in rats. A comparison with the known hepatoprotective agent silymarin revealed that 033 and 033 (2) exhibited higher hepatoprotective potential in most of the parameters with respect to their effect on elevated levels of serum and liver homogenate parameters (Table 1 and 2). Thus the main objective of the present invention is to provide hepatoprotective activity of a bioactive molecule isolated from leaves of *V. negundo* viz., negundoside of formula 1. As shown in the diagram accompanying this specifications Accordingly, the present invention provides hepatoprotective activity of a compound of formula 1 accompanying the specifications which comprises (a) powdering the plant material by known methods;
(b) preparing the aqueous alcoholic extract by percolation;
(c) concentrating the alcoholic extract by conventional method,
(d) removing fatty non polar constituents by triturating the extract with solvents such as ethylene chloride, methylene chloride, chloroform or ethyl acetate;
(e) adsorbing the residue extract over silica gel;
(f) isolation of agnuside from the adsorbed extract by column chromatography;
(g) hepatoprotective activity Characterisation of Negundoside 1

1 obtained as crystalline compound, mp 148-50° C. M+: 496, UV-260 nm (MeOH) nm, (KBr) spectrum showed absorptions at 3400, 1700, 1640 and 1610 cm$^{-1}$. $^1$H NMR (200 MHz, CD$_3$OD) 5 5.48 (J 3, H-1) 7.09 (s, H-3) 25 (m-H-5) 2.19 (m, H-9) 1.25 (s, H-10) 6.80 (dd, 2, 7, H-3", H-5"), 7.83 (d, 2,7, H-2", 6") 4.99 (d,7, H-1') 4.69 (d, J, 7, H-2") $^{13}$C NMR, 122.99 (C-1), 133.67, (C-2",6") 116.92 (C-3",5"), 164.11 (C-4") 168.08 (CO) (95.83 (C-1), 151.98 (C-3), 116.92 (C-4), 30.96 (C-5) 31.98 (C-6) 42.04 (C-7), 80.64 (C-8). 53.19 (C-9) 25.15 (C-10), 170.71 (C-11) 98.64 (C-1'), 76-85 (C-2') 75.70 (C-3'), 72.55 (C-4) 79.30 (C-5') 63.54 (C-6').

DETAILED DESCRIPTION OF THE INVENTION

Accordingly, the present invention provides a method for treating and/or preventing hepatic disease conditions in a subject mammals including human beings, said method comprising the steps of administering to the mammal an effective dosage of composition comprising 2'-p-Hydroxy benzoyl mussaenosidic acid from plant *Vitex negundo* optionally as individual or in combination with one or more pharmaceutically additives.

wherein the said composition reduces the elevated levels of serum glutamin-pyruvic transaminase (GPT) about 70%.

Another embodiment of the present invention wherein the said composition reduces the elevated levels of serum glutamin-oxalo acetic transaminase (GOT) about 60%

In yet another embodiment of the present invention wherein the said composition reduces the elevated levels of serum alkaline phosphatase (ALP) about 60%.

In still another embodiment of the present invention wherein the said composition reduces the elevated levels of serum tryglycerides about 58%.

In yet another embodiment of the present invention wherein said composition against the elevated level of bilirubin up to about 66%.

In still another embodiment of the present invention wherein compound agnuside is obtained from the whole plant.

In yet another embodiment of the present invention wherein 2'-p-Hydroxy benzoyl mussaenosidic acid is of concentration ranging between about 20 to 200 mg/kg-body weight.

In still another embodiment of the present invention wherein 2'-p-Hydroxy benzoyl mussaenosidic is of concentration is about 50 mg/kg-body weight.

In yet another embodiment of the present invention wherein the subject is mammal preferably humans.

In still another embodiment of the present invention said composition is used singly or in combination with pharmaceutically acceptable carriers.

In yet another embodiment of the present invention wherein said composition is administered to subject in combination with pharmaceutically acceptable additives, carriers, diluents, solvents, filters, Lubricants, excipients, binder or stabilizers.

In still another embodiment of the present invention wherein the desired dosage is administered for both preventive and curative properties.

In yet another embodiment of the present invention wherein said composition is administered, orally or by any clinically/medically accepted methods.

In still another embodiment of the present invention wherein the preferred dosage for human beings is about 5 mg/Kg of body weight.

In yet another embodiment of the present invention wherein the dosage is safe for consumption and free of any side effects.

In still another embodiment of the present invention state the various physical forms in which the composition is available, e.g. powder, tablet, capsule, syrup, granules, emulsion, aerosoal, or beads.

In yet another embodiment of the present invention wherein is useful for Liver cirrhosis, Galactosemia, Hemoanigoma, Hemochromatosis, Hepatitis A, Hepatitis B, Hepatitis C, Hepatitis D, Hepatitis E, Hepatitis G, Alcholic Liver disease, Autoimmune hepatitis, Cancer of Liver, Biliary Atresia, Glycogen Storage Disease 1, Alpha-1-antitrypsin deficiency, Alagille syndrome, Byler Disease, Caroli disease, Fatty liver, Itching in Liver, Primar Biliary Cirrhosis, Sclerosing Cholangitis or Protoporphyria Erythroepatic.

One more embodiment of the present invention provides a process for the isolation of compound 2'-p-Hydroxy benzoyl mussaenosidic acid of formula 1, said compound isolated from aerial part/whole body comprising of steps:

1. powdering the plant material by known methods
2. preparing the aqueous alcoholic extract by percolation
3. concentrating the alcoholic extract by conventional method
4. removing fatty non-polar constituents by triturating the extract with solvents such as ethylene chloride, methylene chloride, chloroform or ethyl acetate
5. adsorbing the residue extract over silica gel
6. isolating of 2'-p-Hydroxy benzoyl mussaenosidic acid from the adsorbed extract by column chromatography

BRIEF DESCRIPTION OF THE ACCOMPANYING DRAWINGS

Figure 1:
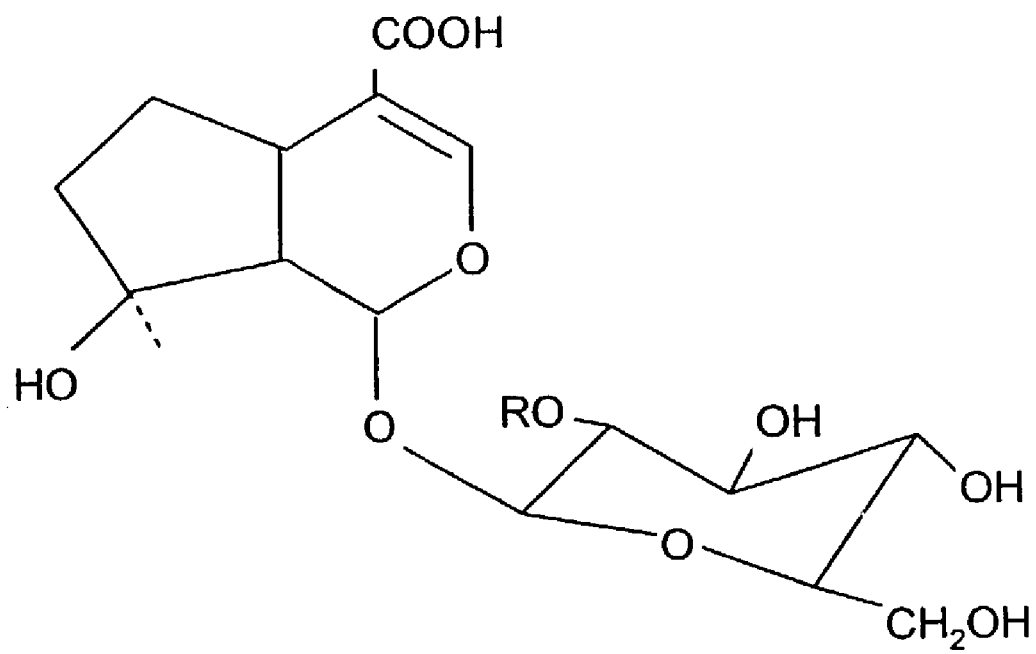
FIG. 1 shows the negundoside.
Figure 1:
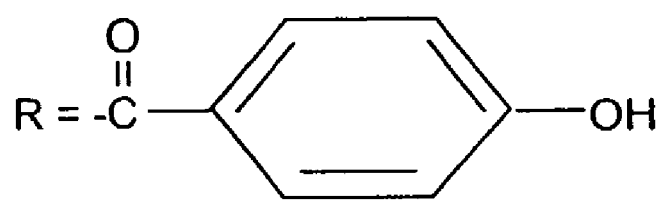
Figure 2:
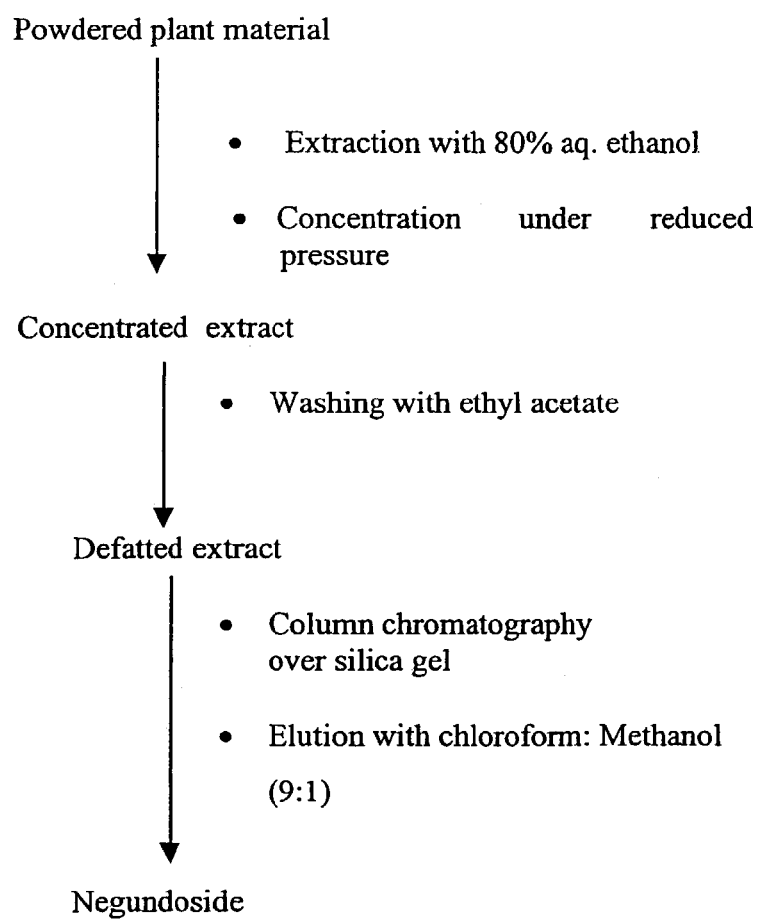
FIG. 2 shows the flow sheet for isolation of 2'-p-hydroxybenzoylmussaenosidie (negundoside).

The following examples are intended to demonstrate some of the preferred embodiments and in no way should be construed so as to limit the scope of the invention. Any person skilled in the art can design more formulations, which may be considered as part of the present invention.

EXAMPLE 1

The shade dried and powdered leaves of *V. negundo* were extracted with 80% ethanol (4+x−3L) by percolation. The pooled extract was concentrated under reduced pressure at below to 1 liter of aqueous concentrate. The aqueous concentrate was washed with ethyl acetate (3×500 ml) and further concentrated to 400 ml. The syrupy residue was adsorbed over silica gel 400 g and allowed to dry at room temperature. The slurry was put on silica gel column and eluted with mixture of chloroform-methane (9:1), furnished 1 (1.5 g) (coded as 033 (2)).

EXAMPLE 2

The finely ground leaves (200 g) of *Vitex negundo* were extracted thrice with petroleum (60-80°) (1 liter for the first extraction and 600 ml each for two subsequent extractions) The drug was freed of solvent at room temperature. It was then extracted with ethanol (1 liter for the first extraction and then thrice with the same solvent 600 ml each time). Evaporation of ethanol in a rotary film evaporator yielded 30 g of extract (coded as 033).

EXAMPLE 3

033 and 033 (2) showed marked hepatoprotective activity in experimentally induced hepatic damage in rodents using CCU as hepatoxin. 033 and 033 (2) reduced the elevated levels of serum OPT, GOT, ALP, bilirubin, TG and liver homogenate lipid peroxidation and increased the GSH level. 033 and 033 (2) were almost as effective as silymarin, reducing the elevated level of GPT by 67.52 & 60.34%, GOT-58.91 'ft 58.05%, ALP-58.26 & 53.95%, Bilirubin- 60.00 & 66.66%, TG-46.47 & 44.19% and in liver homogenate LP-55:71 & 45.85% and GSH-61.42 & 45.56% respectively. The same with silymarin was: 58.44, 51:63, 52,26,57.50,41.30,62.05 & 60.15% respectively. (Table-1).

EXAMPLE 4

On treatment of experimental animals with galactosamine (GaIN) induced hepatic damage the hepatoprotective activity observed with 033 and 033 (2) was 59.58 & 50.75, 56.62 & 43.64, 54.28 & 50.11, 57.71 & 57.57, 57.89 & 44.76 percent in serum GPT, GOT, Bilirubin, ALP, and TG respectively and 67.51 & 38.65, 66-56 & 48.10 percent in liver homogenate lipid peroxidation (LP) and GSH respectively. The same with silymarin was 57.38, 55.40, 60.00. 53.54, 46.17, 69.59, 67.18 percent respectively (Table-2). Advantages of the present invention over currently used plant based hepatoprotectives:

1. Negundoside is more potent man the commercially available herbal hepatoprotective agent silymarin.

2. Silymarin is a mixture of three constituents whose relative proportion varies from batch to batch while negundoside is a pure compound.

TABLE 1

Hepatoprotective activity (in vivo) of 033, 033 (2) and Silymarin fed at 48 h, 24 h, 2 h before and 6 h after CCU (1 ml/kg, p.o.) induced hepatic injury in rats[a].

| Treatment | Dose Mg/kg p.o. | Serum parameters | | | | | Hepatic parameters | |
|---|---|---|---|---|---|---|---|---|
| | | OPT (Units) | GOT (Units) | ALP" | Bilirubin (mg %) | Triglycerides (mg %) | Lipid peroxidation' | Glutathione[d] |
| 033 + CCl$_4$ | 400 | 67.52 | 58.91 | 58.26 | 60.00 | 46.47 | 55.71 | 61.42 |
| 033(2) + CCl$_4$ | 50 | 60.34 | 58.05 | 53.95 | 66.66 | 44.19 | 45.85 | 45.56 |
| Silymarin + CCU | 50 | 58.44 | 51.63 | 52.26 | 57.50 | 41.30 | 62.05 | 60.15 |

[a]Values represent the mean percent hepatoprotective activity of six animals in each group.
H: Hepatoprotective activity was calculated as $\{1 - (T - V/C - V)\} \times 100$ where "T" is mean value of drug and CCl$_4$, "C" is mean value of CCU alone and "V" is the mean value of vehicle treated animals.
Unit: each unit is μ mole pyruvate/min/L.
[b]is n mole of p-nitrophenol formed/min/L,
[c]is n moles MDA/g liver.,
[d]is μ mole GSH/g liver

TABLE 2

Hepatoprotective activity (in vivo) of 033, 033 (2) and Silymarin fed at 48 h, 24 h, 2 h before and 6 h after GaIN (300 mg/kg, s.c.) induced hepatic injury in rats[a].

| Treatment | Dose mg/kg, p.o | Serum parameters | | | | | Hepatic parameters | |
|---|---|---|---|---|---|---|---|---|
| | | OPT (Units) | GOT (Units) | Bilirubin (mg %) | ALP[b] | Triglycerides (mg %) | Lipid peroxidation[c] | Glutathioned |
| 033 + GaIN | 400 | 59.58 | 56.62 | 54.28 | 57.71 | 57.89 | 67.51 | 66.56 |
| 033 (2) + GaIN | 50 | 50.75 | 43.64 | 50.11 | 57.57 | 44.76 | 38.65 | 48.10 |
| Silymarin + GaIN | 50 | 57.38 | 55.40 | 60.00 | 53.54 | 46.17 | 69.59 | 67.18 |

[a]Values represent the mean percent hepatoprotective activity of six animals in each group.
H: Hepatoprotective activity was calculated as $\{1 - (T - V/C - V)\} \times 100$ where "T" is mean value of drug and GaIN, 'C' is mean value of GaIN alone and "V" is the mean value of vehicle treated animals.
Unit: each unit is nmole pyruvate/min/L.
[b]is u, mole of p-nitrophenol formed/min/L,
[c]is n moles MDA/g liver.,
[d]is n mole GSH/g liver

What is claimed:

1. A method for treating hepatic disease conditions in a subject mammal, said method comprising the steps of administering to the mammal an effective dosage of a composition comprising 2'-p-Hydroxy benzoyl mussaenosidic acid isolated from plant *Vitex negundo* optionally as individual or in combination with one or more pharmaceutically acceptable additives, wherein the hepatic disease condition is Galactosemia.

2. The method of claim 1, wherein the said composition reduces the elevated levels of serum glutamin-pyruvic transaminase (GPT) about 70%.

3. The method of claim 1, wherein the said composition reduces the elevated levels of serum glutamin-oxalo acetic transaminase (GOT) about 60%.

4. The method of claim 1, wherein the said composition reduces the elevated levels of serum alkaline phosphatase (ALP) about 60%.

5. The method of claim 1, wherein the said composition reduces the elevated levels of serum tryglycerides about 58%.

6. The method of claim 1, wherein said composition reduces the elevated level of bilirubin up to about 66%.

7. The method of claim 1, wherein 2'-p-Hydroxy benzoyl mussaenosidic acid has a concentration in the range of about 20 to 200 mg/kg-body weight.

8. The method of claim 7, wherein 2'-p-Hydroxy benzoyl mussaenosidic has a concentration in the range of about 50 mg/kg-body weight.

9. The method of claim 1, wherein the subject mammal is human.

10. The method of claim 1, wherein said composition is further used singly or in combination with pharmaceutically acceptable carriers.

11. The method according to claim 1 wherein said composition is administered to the subject in combination with pharmaceutically acceptable additives, carriers, diluents, solvents, filters, lubricants, excipients, binders or stabilizers.

12. The method of claim 1, wherein said composition is administered by any medically accepted methods.

13. The method of claim 1, wherein dosage for mammals is about 5 mg/Kg of body weight.

14. The method of claim 1, wherein the dosage is safe for consumption and free of any side effects.

15. The method of claim 1, wherein the composition is in a form of a powder, a tablet, a capsule, a syrup, granules, an emulsion, an aerosol, or beads.

16. The method of claim 12, wherein said composition is administered orally.

* * * * *